US010858351B2

(12) United States Patent
Baradi et al.

(10) Patent No.: US 10,858,351 B2
(45) Date of Patent: Dec. 8, 2020

(54) SUBSTITUTED TETRAHYDROPYRIDINE DERIVATIVES AS IDO-1 INHIBITORS AND USES THEREOF

(71) Applicant: Alberta Research Chemicals Inc., Edmonton (CA)

(72) Inventors: Praveen Baradi, Edmonton (CA); Damayanthi Yalamati, Edmonton (CA); Rajeshwar Singh, Edmonton (CA)

(*) Notice: Subject to any disclaimer, the term of this patent is extended or adjusted under 35 U.S.C. 154(b) by 0 days.

(21) Appl. No.: 15/893,341

(22) Filed: Feb. 9, 2018

(65) Prior Publication Data

US 2018/0312497 A1    Nov. 1, 2018

Related U.S. Application Data

(60) Provisional application No. 62/490,073, filed on Apr. 26, 2017.

(51) Int. Cl.
| | |
|---|---|
| *C07D 413/14* | (2006.01) |
| *A61K 31/5377* | (2006.01) |
| *A61K 45/06* | (2006.01) |
| *A61P 35/00* | (2006.01) |
| *A61K 31/496* | (2006.01) |
| *A61P 37/00* | (2006.01) |
| *C07D 401/14* | (2006.01) |
| *A61K 31/4545* | (2006.01) |
| *A61P 31/12* | (2006.01) |

(52) U.S. Cl.
CPC ........ *C07D 413/14* (2013.01); *A61K 31/4545* (2013.01); *A61K 31/496* (2013.01); *A61K 31/5377* (2013.01); *A61K 45/06* (2013.01); *A61P 31/12* (2018.01); *A61P 35/00* (2018.01); *A61P 37/00* (2018.01); *C07D 401/14* (2013.01)

(58) Field of Classification Search
CPC .................................................. C07D 413/14
See application file for complete search history.

(56) References Cited

U.S. PATENT DOCUMENTS

| | | | |
|---|---|---|---|
| 5,981,754 | A | 11/1999 | Badone et al. |
| 7,803,792 | B2 | 9/2010 | Sasahara et al. |
| 7,973,030 | B2 | 7/2011 | Sasahara et al. |
| 9,765,018 | B2 | 9/2017 | Markwalder et al. |

FOREIGN PATENT DOCUMENTS

WO    WO-2011031896 A2 *   3/2011   ........... C12N 9/1205

OTHER PUBLICATIONS

"Can cancer be prevented?" (Dec. 2016). Accessed Mar. 31, 2019. Available from: <https://www.cancerresearchuk.org/about-cancer/causes-of-cancer/can-cancer-be-prevented>. (Year: 2016).*
"Prevention and Treatment of Viral Infections." (Feb. 2013). Accessed Mar. 31, 2019), discloses that medicaments can be used to prevent many viral infections (p. 13 of 14. (Year: 2013).*
Palmer, S. "Is There a Link Between Nutrition and Autoimmune Disease?" Today's Dietitian. (Nov. 2011). vol. 13, No. 11, p. 36. Year: 2011).*
Curti, A., et al. "The role of indoleamine 2,3-dioxygenase in the induction of immune tolerance: focus on hematology." Blood. (Mar. 12, 2009), vol. 113, No. 11, pp. 2394-2401. (Year: 2009).*

* cited by examiner

*Primary Examiner* — John S Kenyon
(74) *Attorney, Agent, or Firm* — Bennett Jones LLP

(57) ABSTRACT

Compounds of formula I that modulate or inhibit the enzymatic activity of indoleamine 2,3-dioxygenase, pharmaceutical compositions including such compounds and methods of treating diseases, conditions or disorders utilizing such compounds and compositions.

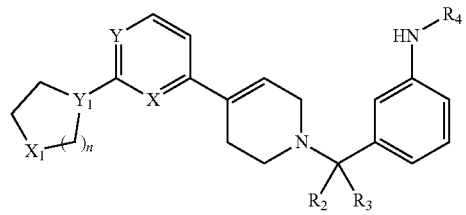

11 Claims, No Drawings

SUBSTITUTED TETRAHYDROPYRIDINE DERIVATIVES AS IDO-1 INHIBITORS AND USES THEREOF

FIELD OF THE INVENTION

The present invention relates to compounds that modulate or inhibit the enzymatic activity of indoleamine 2,3-dioxygenase, pharmaceutical compositions including such compounds, and methods of treating diseases, conditions or disorders utilizing such compounds and compositions.

BACKGROUND

Cancer immunotherapy is currently entering an exciting new era because of the efficacy of immune checkpoint inhibitors (Annu. Rev. Med. 2014, 65, 185-202), adaptive cell therapy with tumor infiltrating lymphocytes and chimeric antigen receptor T-cell therapy. It is widely recognized that these therapies as well as more traditional approaches such as chemotherapy and radiotherapy could be combined in strategies to overcome tumor-induced immunosuppression.

Tryptophan is an essential amino acid supplied in our diet and is required for cell proliferation and survival. Indoleamine-2,3-dioxygenase (IDO) is a heme-containing intracellular enzyme that catalyzes the first and rate-determining step in the degradation of L-tryptophan to N-formyl-kynurenine, which is then metabolized by multiple steps to eventually produce nicotinamide adenine dinucleotide (NAD+). Tryptophan catabolites produced from N-formyl-kynurenine, such as kynurenine, are known to be preferentially cytotoxic to T-cells. Thus, an overexpression of IDO can lead to increased tolerance in the tumor microenvironment. IDO overexpression has been shown to be an independent prognostic factor for decreased survival in cancer patients with melanoma, pancreatic, colorectal and endometrial cancers among others.

Therefore, there is a need in the art for a therapeutic agent which is effective in modulating or inhibiting the function of IDO, which may be an alternative or additional treatment for patients with diseases or conditions affected by the activity of IDO.

This background information is provided merely to provide information believed to be relevant to a basic understanding of the present invention. It is not an admission that any of the foregoing is prior art against any aspect of the claimed invention.

SUMMARY OF THE INVENTION

Aspects of the present invention include novel compounds which modulate or inhibit the enzymatic activity of IDO, methods of modulating or inhibiting the enzymatic activity of IDO in vivo, ex vivo or in vitro, and methods for treating patients, using the compounds described and claimed herein.

The compounds of the invention described herein may be used in the treatment of diseases or disorders associated with or sensitive to the enzymatic activity of IDO, and to make medicaments for the treatment of diseases or disorders associated with or sensitive to the enzymatic activity of IDO.

This invention also encompasses pharmaceutical compositions, single unit dosage forms, dosing regimens and kits which comprise at least one compound described herein.

DETAILED DESCRIPTION

I. Compounds of Present Invention:

In a first aspect, the present invention comprises compounds of Formula (I):

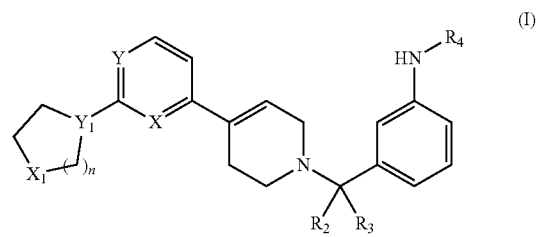

wherein:
X is N or CR;
Y is N or CR and $Y_1$ is N or C;
R is H, halogen, optionally substituted C1-C3 alkyl or optionally substituted C1-C3 alkoxy;
$X_1$ is selected from $CH_2$, O, S or $NR_1$ where $R_1$ is H or C1-C3 alkyl;
n is 1, 2 or 3;
$R_2$ and $R_3$ independently is H or C1-C2-alkyl or, together with the carbon to which they are attached to, form C3-C4 cycloalkyl;
$R_4$ is —$CONHR_5$, —$CSNHR_5$, $C(=NH)NHR_5$, —$SO_2R_6$, —$COR_6$, optionally substituted C1-C6 alkyl, optionally substituted C3-C8 heteroaryl, optionally substituted C3-C8 alkylheteroaryl, optionally substituted C3-C8 alkoxylheteroaryl, optionally substituted C3-C8 heterocycle, optionally substituted C3-C8 alkylheterocycle or optionally substituted C3-C8 alkoxyheterocycle;
$R_5$ is optionally substituted C1-C6 alkyl, optionally substituted C2-C6 alkenyl, optionally substituted C2-C6 alkynyl, optionally substituted C3-C7 cycloalkyl, or optionally substituted C4-C7 cycloalkenyl; optionally substituted aryl, optionally substituted C7-C10 alkylaryl, optionally substituted C7-C10 alkoxyaryl, optionally substituted C3-C10 heteroaryl, optionally substituted C3-10-alkyl heteroaryl or C3-C8 heterocycle;
$R_6$ is $CF_3$, optionally substituted C1-C5 alkyl, optionally substituted aryl, optionally substituted C7-C10 alkylaryl, optionally substituted C7-C10 alkoxyaryl, optionally substituted C3-C10 heteroaryl, optionally substituted C3-10-alkyl heteroaryl or C3-C8 heterocycle.

In another aspect, the invention provides a compound of Formula (II):

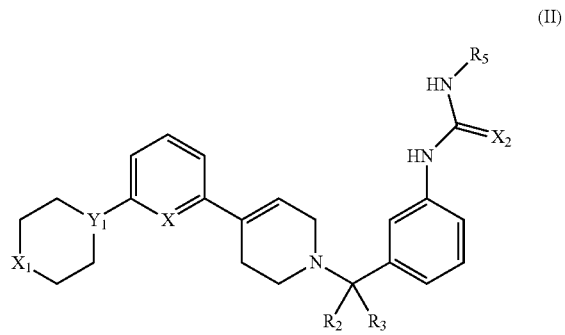

wherein:
  X is N;
  $X_1$ is $CH_2$, O, S or $NR_1$ where $R_1$ is H or C1-C3 alkyl;
  $Y_1$ is N or C;
  $R_2$ and $R_3$ independently is H or C1-C2-alkyl or, together with the carbon to which they are attached to, form C3-C4 cycloalkyl;
  $X_2$ is O, S, or NH;
  $R_5$ is optionally substituted C1-C6 alkyl, optionally substituted C2-C6 alkenyl, optionally substituted C2-C6 alkynyl, optionally substituted C3-C7 cycloalkyl, optionally substituted C4-C7 cycloalkenyl, optionally substituted aryl, optionally substituted C7-C10 alkylaryl, optionally substituted C7-C10 alkoxyaryl, optionally substituted C3-C10 heteroaryl, optionally substituted C3-10-alkylheteroaryl or C3-C8 heterocycle.

For certain compounds of Formula II, any or all of the optional substitutions may be selected from chlorine, fluorine, methyl, methoxy, trifluoromethyl or trifluoromethoxy.

Specific compounds of Formula II may include 1-(3-((4-(6-morpholinopyridin-2-yl)-5,6-dihydropyridin-1(2H)-yl)methyl)phenyl)-3-p-tolylguanidine and 1-cyclohexyl-3-(3-((4-(6-morpholinopyridin-2-yl)-5,6-dihydropyridin-1(2H)-yl)methyl)phenyl)guanidine, In another aspect, the invention comprises a compound of Formula III:

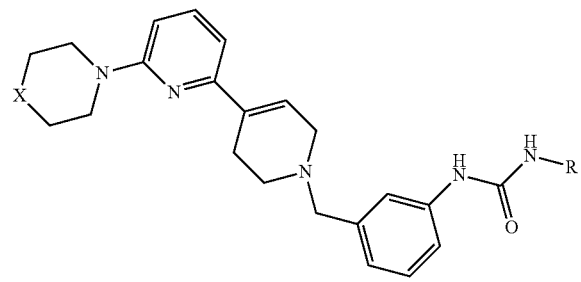

(III)

wherein
  X is $CH_2$, O, S, or $NR_1$ where $R_1$ is H or C1-C3 alkyl;
  R is optionally substituted C1-C6 alkyl, optionally substituted C2-C6 alkenyl, optionally substituted C2-C6 alkynyl, optionally substituted C3-C7 cycloalkyl, or optionally substituted C4-C7 cycloalkenyl; optionally substituted aryl, optionally substituted C7-C10 alkylaryl, optionally substituted C7-C10 alkoxyaryl, optionally substituted C3-C10 heteroaryl, optionally substituted C3-10-alkyl heteroaryl or C3-C8 heterocycle.

In embodiments of Formula III, X is O and R is cyclohexyl; or X is $CH_2$ and R is ethyl; or X is $CH_2$ and R is cyclohexyl; or X is O and R is cyclopropyl.

Specific compounds of Formula III may include:
1-Ethyl-3-[3-(6-morpholin-4-yl-3',6'-dihydro-2'H-[2,4']bipyridinyl-1'-ylmethyl)-phenyl]-urea;
1-Cyclohexyl-3-[3-(6-morpholin-4-yl-3',6'-dihydro-2'H-[2,4']bipyridinyl-1'-ylmethyl)-phenyl]-urea;
1-Ethyl-3-[3-(6-piperidine-1-yl-3',6'-dihydro-2'H-[2,4']bipyridinyl-1'-ylmethyl)-phenyl]-urea;
1-Cyclohexyl-3-[3-(6-piperidine-1-yl-3',6'-dihydro-2'H-[2,4']bipyridinyl-1'-ylmethyl)-phenyl]-urea;
S 1-Cyclopropyl-3-[3-(6-piperidine-1-yl-3',6'-dihydro-2'H-[2,4']bipyridinyl-1'-ylmethyl)-phenyl]-urea;
S 1-Cyclopropyl-3-[3-(6-morpholin-4-yl-3',6'-dihydro-2'H-[2,4']bipyridinyl-1'-ylmethyl)-phenyl]-urea;
1-Cyclopropyl-3-[3-(6-piperzin-1-yl-3',6'-dihydro-2'H-[2,4']bipyridinyl-1'-ylmethyl)-phenyl]-urea;
1-Cyclopropyl-3-{3-[6-(4-methyl-piperazin-1-yl)-3',6'-dihydro-2'H-[2,4']bipyridinyl-1'-ylmethyl]-phenyl}-urea;
S 1-Ethyl-3-{3-[6-(4-methyl-piperazin-1-yl)-3',6'-dihydro-2'H-[2,4']bipyridinyl-1'-ylmethyl]-phenyl}-urea;
1-Cyclohexyl-3-{3-[6-(4-methyl-piperazin-1-yl)-3',6'-dihydro-2'H-[2,4']bipyridinyl-1'-ylmethyl]-phenyl}-urea;
1-[3-(6-Morpholin-4-yl-3',6'-dihydro-2'H-[2,4']bipyridinyl-1'-ylmethyl)-phenyl]-3-p-tolyl-urea;
1-(2,4-Difluoro-phenyl)-3-[3-(6-morpholin-4-yl-3',6'-dihydro-2'H-[2,4']bipyridinyl-1'-ylmethyl)-phenyl]-urea;
1-(4-Chloro-2-fluoro-phenyl)-3-[3-(6-morpholin-4-yl-3',6'-dihydro-2'H-[2,4']bipyridinyl-1'-ylmethyl)-phenyl]-urea;
1-(2-Fluoro-phenyl)-3-[3-(6-morpholin-4-yl-3',6'-dihydro-2'H-[2,4']bipyridinyl-1'-ylmethyl)-phenyl]-urea;
1-[3-(6-Morpholin-4-yl-3',6'-dihydro-2'H-[2,4']bipyridinyl-1'-ylmethyl)-phenyl]-3-p-tolyl-thiourea;
1-Cyclohexyl-3-{3-[1-(6-morpholin-4-yl-3',6'-dihydro-2'H-[2,4']bipyridinyl-1'-yl)-ethyl]-phenyl}-urea;
1-Cyclohexyl-3-{3-[1-(6-morpholin-4-yl-3',6'-dihydro-2'H-[2,4']bipyridinyl-1'-yl)-cyclopropyl]-phenyl}-urea;
1-(3-Methyl-isoxazol-5-yl)-3-{3-[1-(6-morpholin-4-yl-3',6'-dihydro-2'H-[2,4']bipyridinyl-1'-yl)-cyclopropyl]-phenyl}-urea;
1-(3-Methyl-isoxazol-5-yl)-3-[3-(6-morpholin-4-yl-3',6'-dihydro-2'H-[2,4']bipyridinyl-1'-ylmethyl)-phenyl]-urea; or
1-(5-Methyl-pyridin-2-yl)-3-[3-(6-morpholin-4-yl-3',6'-dihydro-2'H-[2,4']bipyridinyl-1'-ylmethyl)-phenyl]-urea.

Any of the optional substitutions referred to herein may be selected, without limitation, from the following: halogen such as chlorine, fluorine, bromine or iodine; alkyl groups such as methyl, ethyl, n-propyl, isopropyl, n-butyl, isobutyl, t-butyl, n-pentyl, isopentyl, neopentyl and the alike; alkenyl groups such as ethenyl, propenyl, butenyl, 1-methyl-2-buten-1-yl, heptenyl, octenyl and the like; alkynyl groups such as ethynyl, 1-propynyl, 1-butynyl, heptynyl, octynyl and the like; cycloalkyl groups such as cyclopropyl, cyclobutyl, cyclopentyl, cyclohexyl, cycloheptyl and the like; cycloalkenyl such as cyclobutenyl, cyclopentenyl, cyclohexenyl, cycloheptenyl and the like; alkoxy groups such as methoxy, ethoxy, propyloxy, butoxy and the like; aryl groups such as phenyl, biphenyl, indanyl, 1-naphthyl, 2-naphthyl, terahydronaphthyl. benzyl, phenethyl and the like; heteroaryl such as pyridyl, pyrimidinyl, pyridazinyl, furyl, quinolyl, isoquinolyl, thienyl, imidazolyl, thiazolyl, indolyl, oxazolyl, benzofuryl, benzothienyl, benzthiazolyl, isoxazolyl, pyrazolyl, indazolyl, 1,2,4-thiadiazolyl, isothiazolyl, benzimidazolyl, indolinyl, benzodioxolanyl, benzodioxane and the like; alkylheteroaryl groups where heteroaryl is substituted with methyl, ethyl, isopropyl, or t-butyl group, and the like; alkoxyheteroaryl groups where heteroaryl is substituted with methoxy, ethoxy, propyloxy, butoxy group and the like; heterocycle may be selected from piperazinyl, piperidinyl, morphonyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydroquinoxalinyl, 1,2,3,4-tetrahydro-quinazolinyl and the like; alkylheterocycle groups where a heterocycle is substituted with methyl, ethyl, isopropyl, or t-butyl group and the like; alkoxyheterocycle groups where a heterocycle is substituted with methoxy, ethoxy, propyloxy, butoxy and the like.

Any optional substitution may be any one of or any combination of the specific substitutions described above. In some embodiments, substitutions may be methyl, ethyl, methoxy, ethoxy, chlorine, fluorine, cyano, trifluoromethyl or trifluoromethoxy.

Compounds described herein may exist as geometric isomers (i.e. cis-trans isomers), optical isomers or stereoisomers, such as diastereomers, as well as tautomers. Accordingly, it should be understood that the structural formulae shown includes each and every individual isomer corresponding to the structural formula, including cis-trans isomers, stereoisomers and tautomers, as well as racemic mixtures of these and pharmaceutically acceptable salts thereof. Hence, the definition of any compound is also intended to encompass all R- and S-isomers of a chemical structure in any ratio, e.g. with enrichment (i.e. enantiomeric excess or diastereomeric excess) of one of the possible isomers and corresponding smaller ratios of other isomers.

Diastereoisomers, i.e. non-superimposable stereochemical isomers, can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. Optically active compounds can likewise be obtained by utilizing optically active starting materials and/or by utilizing a chiral catalyst. These isomers may be in the form of a free acid, a free base, an ester or a salt.

The compound described herein may be provided in any form suitable for the intended administration, in particular including pharmaceutically acceptable salts, solvates and prodrugs. Pharmaceutically acceptable salts refer to salts of the compounds, which are considered to be acceptable for clinical and/or veterinary use. Typical pharmaceutically acceptable salts include those salts prepared by reaction of the compounds with a mineral or organic acid or an organic or inorganic base. Such salts are known as acid addition salts and base addition salts, respectively. It will be recognized that the particular counter-ion or multiple counter-ions forming a part of any salt is not of a critical nature, so long as the salt as a whole is pharmaceutically acceptable and as long as the counter-ion does not contribute undesired qualities to the salt as a whole. These salts may be prepared by methods known to the skilled person.

Examples of pharmaceutically acceptable addition salts include acid addition salts formed with inorganic acids e.g. hydrochloric, hydrobromic, sulfuric, nitric, hydroiodic, metaphosphoric, or phosphoric acid; and organic acids e.g. succinic, maleic, acetic, fumaric, citric, tartaric, benzoic, trifluoroacetic, malic, lactic, formic, propionic, glycolic, gluconic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), ethanesulfonic, pantothenic, stearic, sulfinilic, alginic and galacturonic acid; and arylsulfonic, for example benzenesulfonic, p-toluenesulfonic, oxalic, methanesulfonic or naphthalenesulfonic acid; and base addition salts formed with alkali metals and alkaline earth metals and organic bases such as N,N-dibenzylethylenediamine, chloroprocaine, choline, diethanolamine, ethylenediamine, meglumine (N-methylglucamine), lysine and procaine; and internally formed salts.

The compounds described herein may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like.

The compound described herein may be provided as a prodrug. The term "prodrug" used herein is intended to mean a compound which, upon exposure to certain physiological conditions, will liberate the compound described herein, which then will be able to exhibit the desired biological action. Typical examples include a labile carbamate of an amine, a trialkylsilyl ether of an alcohol or a trialkylsilyl ester of an acid, each optionally being trimethylsilyl.

II. Methods of Preparation:

The compounds described herein can be synthesized using the methods described below, together with synthetic methods known in the art of synthetic organic chemistry, or by variations thereon as appreciated by those skilled in the art. Preferred methods may include, but are not limited to, those described below. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The compounds described herein may be prepared using the synthetic scheme as outlined in Scheme 1. The reaction conditions such as temperature, time, choice of solvent and workup procedures are selected which may be suitable for experimental conditions recognized by one skilled in the art. Restrictions to the substituents that are compatible with the reaction conditions will be readily apparent to one skilled in the art and alternate or analogous methods must then be used.

Protection and de-protection in the processes below may be carried out by procedures generally known in the art (see, for example, Greene, T. W. et al, *Protecting Groups in Organic Synthesis,* 3rd Edition, Wiley (1999)). General methods of organic synthesis and functional group transformations are found in: Trost, B. M. et al, eds., *Comprehensive Organic Synthesis: Selectivity, Strategy & Efficiency in Modern Organic Chemistry,* 1$^{st}$ Edition, Pergamon Press, New York, N.Y. (1991); March, J., Advanced Organic Chemistry.

One synthesis may start with commercially available raw material, protected piperidinone (1) which becomes tetrahydropyridinone core unit and two cyclic systems (2) and (3) that constitute part of the tricyclic ring system of all the compounds of the present invention. The two initial intermediates 8 and 13 are prepared according to Schemes 1 and 2.

As shown in Scheme 1, the boron pinacolate intermediate 3 is prepared starting from raw material 1 in two steps and the bromocompound 6 is prepared in one step by known methods. Treatment of compounds 6 with compound 3 under standard palladium coupling conditions such as a Pd(II) catalyst Pd(OAc)$_2$ in a solvent such as THF, afford compounds 7 which upon treatment with strong acids such as TFA or HCl in dioxane provide 8 (Intermediate 1).

SCHEME 1:

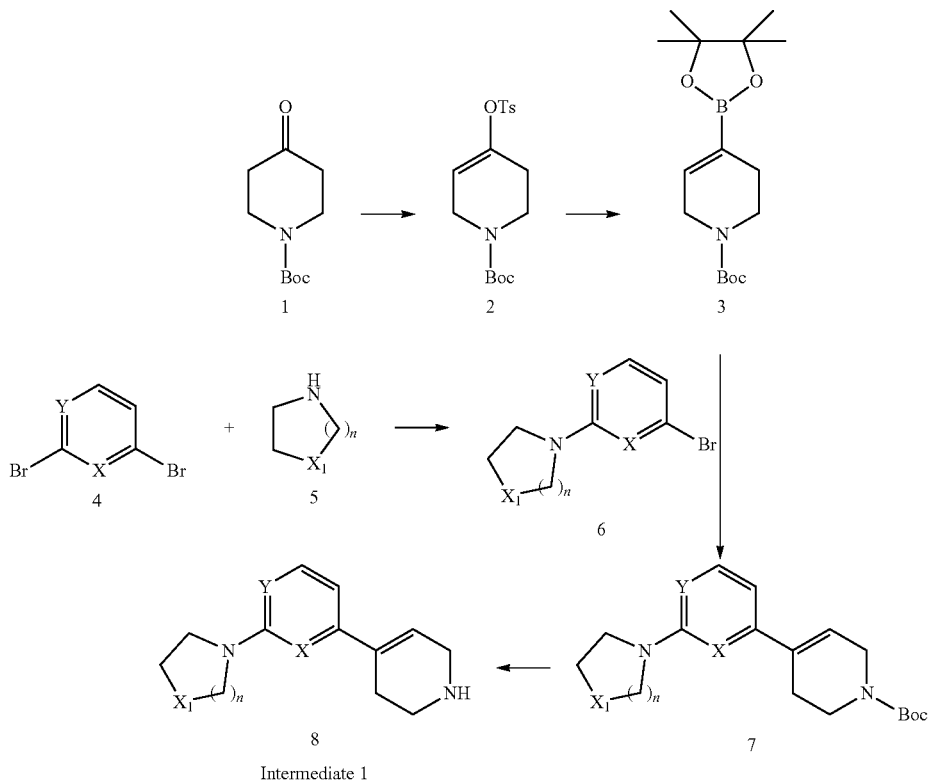

Intermediate 1

Commercially available compound 9 treated with an appropriate organometallic reagent followed by alkylation to afford compound 10 where $R_2$ or $R_3$ provide variations to the molecule. These reactions are well known to those skilled in the art and comprise an alkyl or aryl Grignard reagent such as $R_2$—MgBr or $R_3$—MgBr. The nitroaromatic compounds 10 can be reduced under reductive conditions with Pd/C under an atmospheric pressure or under hydrogen pressure and in a solvent such as ethyl acetate or methanol to afford saturated aniline compounds 11. Selective protection of amine on compound 11 can be achieved under conditions as described above afford compound 12 which upon mesylation with mesyl chloride afford 13 (Intermediate 2).

SCHEME 2:

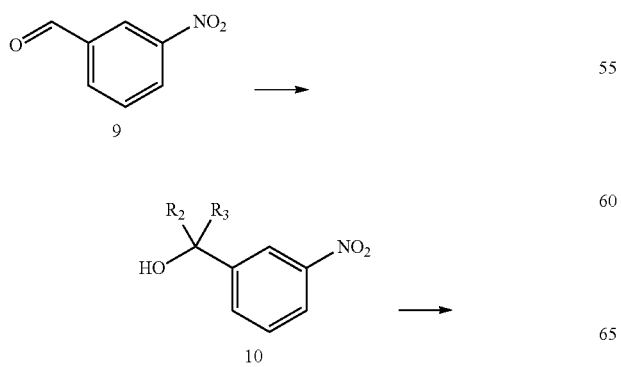

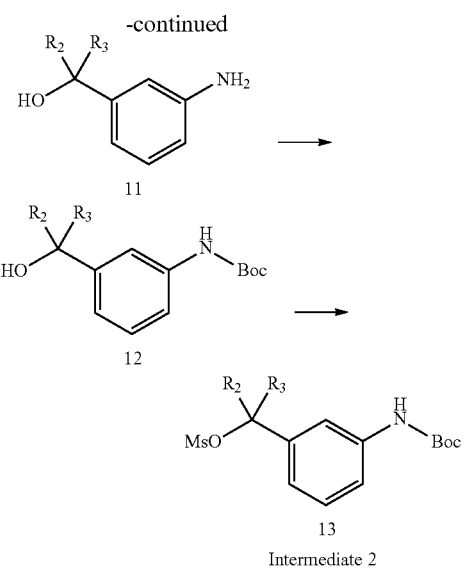

Intermediate 2

Compound 14 is prepared from coupling of Intermediates 1 and 2 in a suitable solvent and in the presence of a suitable base between ambient temperature and boiling point of the solvent. Aniline 15 is prepared from compound 14 after removal of protecting group and is used as the common intermediate for synthesis of compounds of Formula I (16-24).

Treatment of aniline 15 with a commercially available isocyanate, $R_5$—N=C=O, afford urea compounds 16, whereas treatment with commercially available R$_5$—N=C=S, afford thiourea compounds 17, and treatment with R$_5$—NCN in methanolic HCl afford guanidine compounds 18. Typically, these reactions are performed in a solvent such as THF at a temperature between ambient and the boiling point of the solvent. Further treatment of compounds 16, 17 and 18 with beta keto alkyl bromides, R$_4$—CO—CH$_2$—Br, in presence of a base produce corresponding oxazolines (19), thiozolines (20) and imidazoles (21).

SCHEME-3:

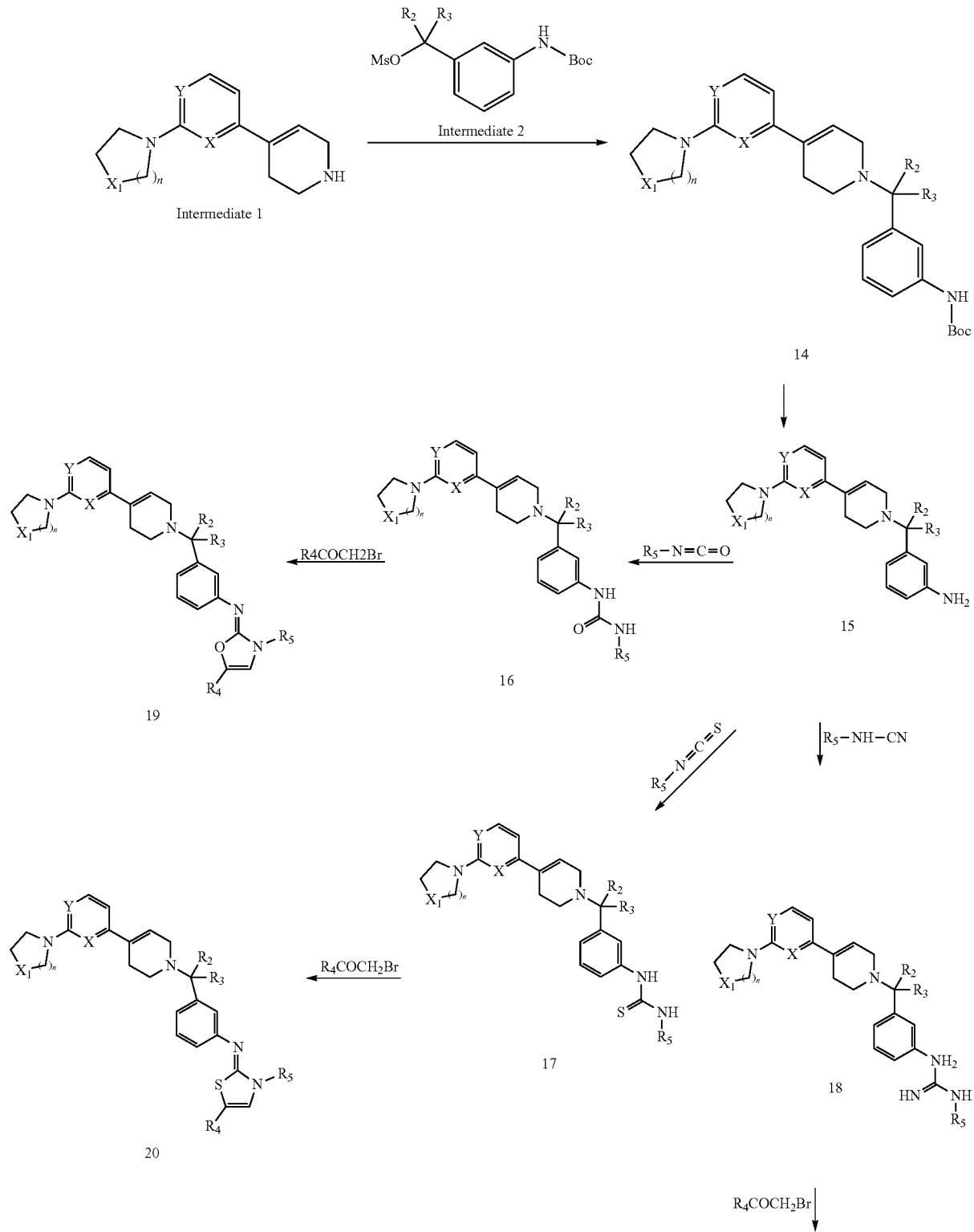

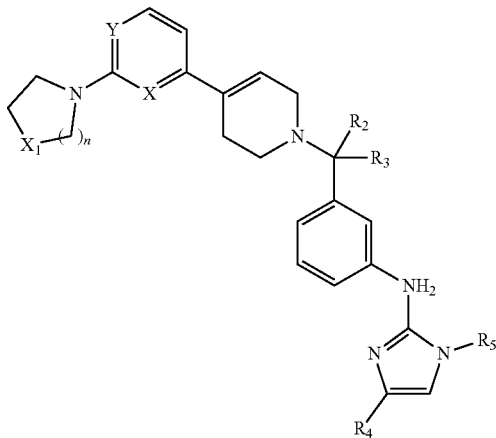

21

As shown below in Scheme 4, compounds 15 (prepared by the methods described above) may be coupled with carboxylic acids using peptide coupling reagents such as Bop, PyBop, HATU or a similar reagent and a suitable base in a solvent such as THF, DMF, NMP, or the like to afford a compound of Formula I (24). The use of such peptide coupling reagents has been reviewed by Han, S-Y et al, Tetrahedron, 60:2447-2467 (2004). Suitable bases include, but are not limited to aliphatic tertiary amines. Alternatively, amines (15) could react with acid chlorides of the formula $R_6COCl$ or acids $R_6COOH$ to give amides (24) or sulphonyl chloride of the formula $R_6SO_2Cl$ to give sulphonamide (23) or with $R_6L$ (L is leaving group) to give compound 22 in suitable solvent and in the presence of a suitable base.

SCHEME 4

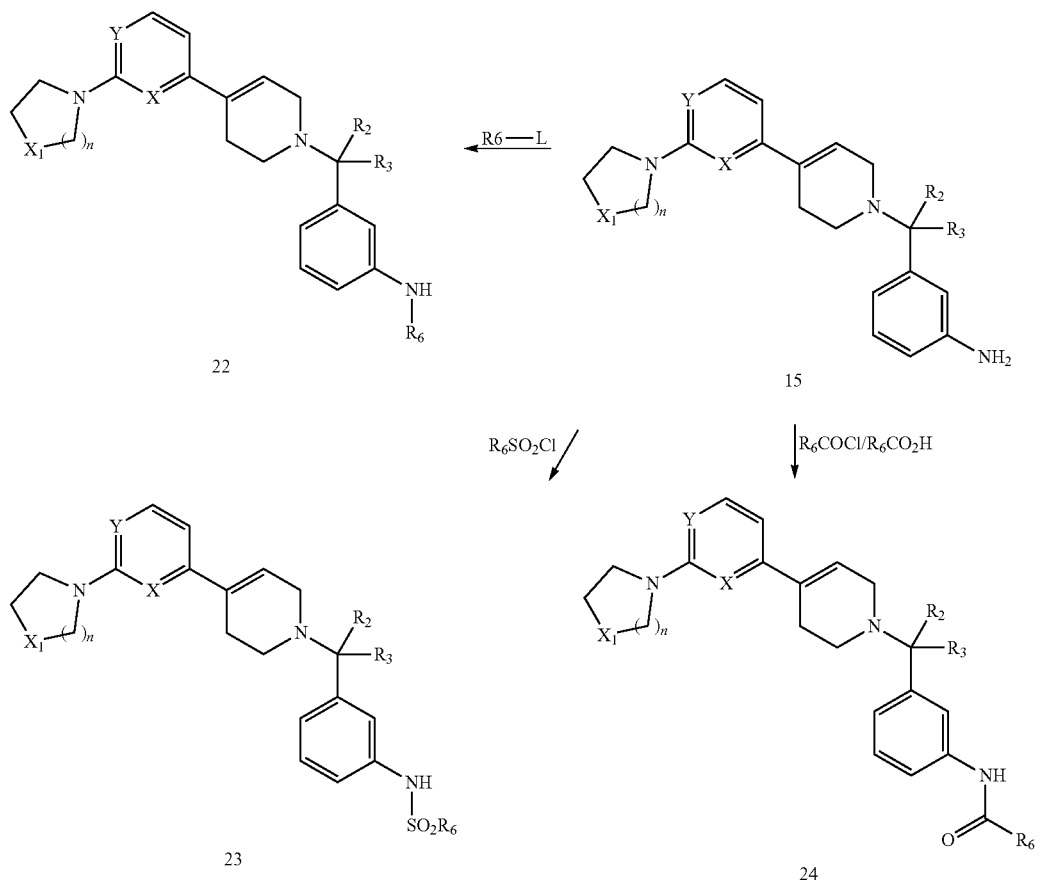

A suitable solvent used in above reaction may be acetonitrile, tetrahydrofuran, ethanol, methanol, chloroform, methylene chloride, pyridine, picoline, N-methylpyrrolidin-2-one, water, dimethylsulphoxide, dimethylformamide or the like, or mixtures thereof.

The reaction temperature may be selected from a range from about −80° to about 250° C. and the reaction time may be selected from a range from about 1 hour to about 96 hours.

III. Therapeutic Applications

The present invention may comprise methods of treating diseases associated with activity or expression, including abnormal activity and/or overexpression, of IDO in a patient by administering to an individual in need of such treatment a therapeutically effective amount or dose of a compound or a pharmaceutical composition described herein. Examples of such diseases can include any disease, disorder or condition that is directly or indirectly linked to expression or activity of the IDO enzyme, such as overexpression or abnormal activity. An IDO-associated disease can also include any disease, disorder or condition that can be prevented, ameliorated, treated or cured by modulating IDO enzyme activity. Examples of IDO-associated diseases include cancer, viral infection such as HIV infection and HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parentally.

The compounds and pharmaceutical compositions described herein may be used in methods of inhibiting immunosuppression such as IDO-mediated immunosuppression in a patient by administering to the patient an effective amount of such a compound or composition. IDO-mediated immunosuppression has been associated with, for example, cancers, tumor growth and metastasis, viral infection, and viral replication.

Types of cancers that may be treated with the compounds or compositions described herein may include, but are not limited to, brain cancers, skin cancers, bladder cancers, ovarian cancers, breast cancers, gastric cancers, pancreatic cancers, prostate cancers, colon cancers, blood cancers, lung cancers and bone cancers. One or more additional therapeutic agents or treatment methods such as, for example, chemotherapeutics or other anti-cancer agents, immune enhancers, immunosuppressants, or radiation can be optionally used in combination with a compound of the present invention for treatment of IDO-associated diseases, disorders or conditions. The additional therapeutic agents can be combined with a compound in a single dosage form, or the agents can be administered simultaneously or sequentially as separate dosage forms. The combination may include two or more compounds of the present invention.

Compounds described herein can modulate activity of IDO. The term "modulate" is meant to refer to an ability to increase or decrease activity of IDO. Accordingly, IDO activity may be modulated by contacting the enzyme with any one or more of the compounds or compositions described herein. In some embodiments, the compounds can act as inhibitors of IDO. In some embodiments, the compounds can be used to modulate activity of IDO in a cell or in an individual in need of modulation of the enzyme by administering a modulating (inhibiting or enhancing) amount of a compound of the invention.

The present invention may comprise methods of inhibiting the degradation of tryptophan in a system containing cells expressing IDO such as a tissue, a living organism, or a cell culture. In some embodiments, the present invention provides methods of altering (e.g., increasing) extracellular tryptophan levels in a patient by administering an effective amount of a compound of composition provided herein. Methods of measuring tryptophan levels and tryptophan degradation are routine in the art.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

Compounds of the present invention may be an "IDO inhibitor", which refers to a compound or therapeutic agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity, such as by forming a covalent bond with the enzyme.

In one embodiment, the invention provides a method of treating an autoimmune disease by providing to a patient in need thereof a compound or composition described herein. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membranoproliferative glomerulonephritis type II, endocrine diseases such as type-I diabetes, autoimmune polyendocrinopathy candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional therapeutic agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds described herein for treatment of IDO-associated diseases, disorders or conditions. The agents can be combined with the present compounds in a single dosage form, or the agents can be administered simultaneously or sequentially as separate dosage forms.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, for example, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide, YERVOY® or Nivolumab. Compounds described herein may also be combined with immunotherapy drugs, including cytokines such as interferon alpha, interleukin 2, and tumor necrosis factor (TNF) in the treatment of melanoma.

Compounds described herein may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or antigenic parts of melanoma cells may be injected into a patient to stimulate the body's immune system to destroy melanoma cells.

Melanomas that are confined to the arms or legs may also be treated with a combination of therapeutic agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents may further include, for example, certain natural products and their derivatives, such as vinca alkaloids, antitumor antibiotics, enzymes, lymphokines and epipodophyllotoxins, vinblastine, Vincristine, vindesine, bleomycin, dactinomycin, daunorubicin, doxorubicin, epirubicin, idarubicin, mitomycin-C, L-asparaginase, interferons (especially IFNO), etoposide, and teniposide.

Other cytotoxic agents include navelbene, CPT-11, anastrazole, letrazole, capecitabine, reloxafine, and droloxafine. Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur, and haematopoietic growth factors.

Other anti-cancer agents include antibody therapeutics such as trastuzumab (HERCEPTIN®), antibodies to costimulatory molecules such as CTLA-4, 4-1BB and PD-1, or antibodies to cytokines (IL-10 or TGF-5).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Other anti-cancer agents also include anti-cancer vaccines comprising dendritic cells, synthetic peptides, DNA vaccines and recombinant viruses.

Compounds described herein may be adminstered together with at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®), SSI-774) and antibodies (Imclone: C225, and Abgenix; ABXEGF); (iii) her-2/neu receptor inhibitors such as farnesyl transferase inhibitors (FTI) such as, for example, L-744,832; (iv) inhibitors of Akt family kinases or the Akt pathway, such as, for example, rapamycin, (v) cell cycle kinase inhibitors such as, for example, flavopiridol and UCN-01; and (vi) phosphatidylinositol kinase inhibitors such as, for example, LY294002. The at least one STI and at least one IDO inhibitor may be in the same or separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention may further provide a pharmaceutical composition for the treatment of a chronic viral infection in a patient comprising at least one compound described herein, optionally, at least one chemotherapeutic drug, and, optionally, at least one antiviral agent, in a pharmaceutically acceptable carrier. The pharmaceutical compositions may include at least one IDO inhibiting compound described herein in addition to at least one other IDO inhibitor, which may be an established or previously known inhibitor. This pharmaceutical composition may also be used in a method for treating a chronic viral infection in a patient by administering an effective amount of the composition.

Chronic viral infections that may be treated using a combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV). Notably, parasitic infections (e.g., malaria) may also be treated by the above methods wherein compounds known to treat the parasitic conditions are optionally added in place of the antiviral agents.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs. Examples of suitable NRTIs include zidovudine (AZT); didanosine (ddI); zalcitabine (ddC); stavudine (d.4T); lamivudine (3TC); abacavir (1592U89); adefovir dipivoxil [bis(POM)-PMEA]; lobucavir (BMS-180194); BCH-IO652; emitricitabine [(−)-FTC]; beta-L-FD4 (also called beta-LD4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4(1H,3H)-pyrimidinedione); and (+)-calanolide A (NSC675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234.475): DMP-450; BMS-2322623; ABT378; and AG-1549. Other antiviral agents include hydroxyurea, ribavirin, IL-2, IL-12, pentafuside and Yissum Project No. 11607.

In yet another embodiment, a compound described herein may be administered to a patient to prevent arterial restenosis, such as after balloon endoscopy or stent placement. In a particular embodiment, the compound may be administered together with at least one taxane (e.g., paclitaxel (Taxol).

The present invention may comprise pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound(s) described herein. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

In any embodiment involving therapy with a combination of therapeutic agents, it is intended to embrace administration of therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

IV. Pharmaceutical Compositions and Dosing

The invention also provides pharmaceutically acceptable compositions which comprise a therapeutically effective amount of one or more of the compounds described herein, formulated together with one or more pharmaceutically acceptable carriers (additives) and/or diluents, and optionally, one or more additional therapeutic agents. While it is possible for a compound described herein to be administered alone, it is preferable to administer the compound as a pharmaceutical composition.

The compounds of this invention can be administered for any of the uses or methods described herein by any suitable means, for example, orally, such as tablets, capsules (each of which includes sustained release or timed release formulations), pills, powders, granules, elixirs, suspensions (including nano suspensions, micro suspensions, spray-dried dispersions), syrups, and emulsions; sublingually; parenterally, such as by subcutaneous, intravenous, intramuscular injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

The dosage regimen for the compounds described herein will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. The selected dosage level may also depend on the additional factors including the activity of the particular compounds and pharmaceutical compositions described herein, whether an ester, salt or amide substituent is of the compound is used, the time of administration, the rate of excretion or metabolism of the particular compound being employed, the rate and extent of absorption, the duration of the treatment, other drugs that may be administered to the patient, compounds and/or materials used in combination with the particular compound employed and like factors well known in the medical arts.

Generally, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in multiple divided doses, such as two, three, or four times daily.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. Actual dosage levels of the active ingredients in the pharmaceutical compositions of this invention may be varied so as to obtain an amount of the active ingredient which is effective to achieve the desired therapeutic response for a particular patient, composition, and mode of administration.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

EXAMPLES

The present invention is described with reference to the following Examples. These Examples are provided for the purpose of illustration only.

In these Examples, melting points were not corrected. All air and moisture sensitive reactions were performed under nitrogen atmosphere. All dry solvents including anhydrous THF, DMF and dichloromethane were purchased from Sigma Aldrich. Isocyanates were purchased from Combi-Blocks. ACS grade solvents were purchased from Fisher and Caledon and used for work-up and column chromatography without distillation. TLC plates (silica gel 60 F254, thickness 0.25 mm, Merck) were purchased from VWR and visualized under UV light as well as stains such as CAM (cerium sulfate-ammonium molybdate) solution, $KMnO_4$ (potassium permanganate) solution, PMA (phosphomolybdic acid) solution and ninhydrine solution. Flash silica gel 60 was purchased from Silicycle, Canada. All compounds were characterized by 1H NMR and ESMS. NMRs were recorded on 400 Varian 400 MHz spectrometers with TMS as internal standard for proton chemical shifts. Electron-spray mass spectrometric analyses were performed Agilent LCMS spectrometer.

Abbreviations used for common chemicals, solvents and reagents are those commonly used and readily recognizable by those skilled in the art.

Commercially available 4-oxo-piperidin-1-carboxylic acid-tert.butylester (1) is a raw material for all the examples and the boronic ester (3) is an early common intermediate used to introduce the tetrahydropyridine unit in the synthesis of series of compounds of interest in the current invention. Intermediates 1 and Intermediate 2 are the core intermediates that can bring left hand side modifications to the molecules of interest. Intermediate 15 is the core intermediate that allows the right hand side modifications with various different functionalities.

Preparation of the Intermediate 1 (Scheme 1):

Preparation of 4-Trifluoromethanesulfonyloxy-3,6-dihydro-2H-pyridine-1-carboxylic acid tert-butyl ester (2). A 1.6 M solution of n-butyllithium in hexanes (6.9 ml, 11 mmol) was added to a stirred solution of diisopropylamine (1.5 ml, 11 mmol) in THF at −78° C. and the mixture stirred for 30 minutes. A solution of 4-oxo-piperidin-1-carboxylic acid-tert.butylester, 1 (2.0 g, 10 mmol) in THF was added and after 30 minutes N-phenyltriflamide (3.9 g, 11 mmol) was added. The mixture was slowly brought to room temperature and stirred at room temperature for 3 hours. The reaction was quenched with water and extracted with ethylacetate. The organic layer separated, washed once with brine and dried over sodium sulfate, filtered and concentrated under reduced pressure. The residue was treated with hexane and removed the solids. The hexane layer was concentrated and purified by column chromatography using 2-5% ethylacetate in hexane to give the title compound 2 (3.01 g, 83 percent). $C_{11}H_{16}F_3NO_5S$ (331.309). ES-MS (m/z): found 332.2 (M+H). $^1$HNMR (400 MHz, DMSO-d6): δ (ppm) 1.48 (s, 9H), 2.44 (m, 2H), 3.63 (t, 2H), 4.04 (d, 2H), 5.76 (s, 1H).

Preparation of 4-(4,4,5,5-Tetramethyl-[1,3,2]dioxaborolan-2-yl)-3,6-dihydro-2H-pyridine-1-carboxylic acid tert-butyl ester (3)

A degassed mixture of compound (2) (2.0 g, 6.04 mmol), bis(pinacolato)diboron (1.68 g, 6.64 mmol), KOAc (1.8 g, 18.11 mmol), Pd(dppf)Cl$_2$ (132 mg, 0.81 mmol), dppf (100 mg, 0.81 mmol) and 50 mL of 1,4-dioxane was stirred at 80° C. overnight. Dioxane was removed from the reaction mixture and was poured onto water (100 mL) and extracted with EtOAc (200 mL). The organic layer was washed with water (100 mL) and brine (100 mL), dried over Na$_2$SO$_4$, concentrated and purified by silica gel column using 5% ethylacetate in hexane system to give compound (3) (1.17 g, 63%) as a white solid. C$_{16}$H$_{28}$BNO$_4$ (309.21). ES-MS (m/z): found 310.2 (M+H). TLC: Rf=0.4 (10% ethylacetate in hexane). $^1$HNMR (400 MHz, CDCl3): δ ppm, 6.45 (s, 1H), 3.94 (d, J=2.7 Hz, 2H), 3.62 (t, J=5.6 Hz, 2H), 2.22 (s, 2H), 1.45 (s, 9H), 1.25 (s, 12H).

Preparation of 4-(6-Bromo-pyridin-2-yl)-morpholine (6A) (X=N; Y=C; X$_1$=O; n=2, Scheme 1)

In a 100 mL round bottom flask 2,6-dibromopyridine (4, X=Y=C), 1 g, 4.22 mmol), Morpholine, (n=2, X$_1$=O) (400 mg, 4.64 mmol), anhydrous potassium phosphate (0.896 g, 4.22 mmol) were taken in dry 1,4-Dioxane (60 ml) and degassed with a strong stream of nitrogen for at least 10 min. Then the reaction was heated at 105° C. under inert conditions for 16 h, cooled to room temp, solvents were removed under vacuum, residue was diluted with water, partitioned in DCM and water. The organic layer was washed with brine, dried over sodium sulfate, filtered and concentrated under vacuum to give crude product which was purified by flash chromatography using silica gel column (8:2 Hex/EtOAc) to give pure 4-(6-Bromo-pyridin-2-yl)-morpholine, 6A (600 mg, 60%). C9H11BrN2O. (243.1) ES-MS (m/z): found 243.9 (M+H). TLC: Rf=0.25 (20% ethylacetate in hexane). $^1$H-NMR (400 MHz, DMSO-d6) δ ppm, 3.6 (4H, m) 3.7 (4H, m) 6.9 (1H, m) 7.3 (1H, m) 7.7 (1H, M) 7.9 (2H, m) 8.1 (2H, m).

Preparation of 6-Morpholin-4-yl-3',6'-dihydro-2'H-[2,4']bipyridinyl-1'-carboxylic acid tert-butyl ester (7A)

Tert-butyl 4-(4,4,5,5-tetramethyl-1,3,2-dioxaborolan-2-yl)-5,6-dihydropyridin-1(2H)-carboxylate (3) (747 mg, 2.42 mmol), 4-(6-bromopyridin-2-yl)morpholine (6) (533 mg, 2.20 mmol), Pd(dppf)Cl$_2$ (81 mg, 0.11 mmol), and Cs$_2$CO$_3$ (1.5 g, 4.40 mmol) were added to toluene (15 mL) and purged with nitrogen. The reaction mixture was stirred at 110° C. overnight, cooled and solvents were removed under reduced pressure. The residue was purified by silica gel column chromatography to give the desired compound (7A) (101 mg, 13%). C19H27N3O3 (345.44). ES-MS (m/z): found 367.2 (M+Na). $^1$H NMR (400 MHz, CDCl$_3$) δ 7.58-7.44 (m, 1H), 6.77 (d, J=7.4 Hz, 1H), 6.64 (s, 1H), 6.54 (d, J=8.4 Hz, 1H), 4.26-4.08 (m, 2H), 3.96-3.78 (m, 4H), 3.64 (t, J=5.6 Hz, 2H), 3.60-3.49 (m, 4H), 2.62 (s, 2H), 1.58-1.43 (s, 9H).

Preparation of 6-Morpholin-4-yl-1',2',3',6'-tetrahydro-[2,4']bipyridinyl hydrochloride (8A) (Intermediate 1)

6-Morpholin-4-yl-3',6'-dihydro-2'H-[2,4']bipyridinyl-1'-carboxylic acid tert-butyl ester (7A, 98 mg) was stirred with 4% HCl in Dioxane (10 ml) for 2 hours and removed solvents under reduced pressure. The resulting white solid, hydrochloride salt (8A) was used as it is in the next step without further purification. C14H20ClN3O (281.78). ES-MS (m/z): found 293.1 (M+H). 1HNMR: $^1$H NMR (400 MHz, DMSO-D6) δ 9.53 (s, 2H), 7.62 (dd, J=31.5, 23.7 Hz, 1H), 6.87 (d, J=7.4 Hz, 1H), 6.78 (d, J=8.5 Hz, 1H), 6.63 (s, 1H), 3.69-3.79 (m, 6H), 3.53-3.40 (m, 4H), 3.23 (s, 2H), 2.68 (d, J=21.0 Hz, 2H).

Preparation of Intermediate 2 (Compound 13, R$_2$=R$_3$=H, Scheme 2):

Preparation of (3-Hydroxymethyl-phenyl)-carbamic acid tert-butyl ester (12): (3-Amino-phenyl)-methanol (11) (R$_2$=R$_3$=H, Scheme 2) (5.0 g, 40.6 mmol) was suspended in tetrahydrofuran (50 mL) and ditert-butyl dicarbonate (9.8 g, 44.6 mmol) was added. The solids quickly dissolved with stirring and the resulting solution was heated to 80° C. for 5 h and then at 25° C. for 16 h. The solution was concentrated in vacuo to give thick yellow oil. Purification flash column chromatography using 10-20% ethyl acetate in hexanes to afford (3-hydroxymethyl-phenyl) carbamic acid tert-butyl ester (12) (11 g, quantitative) as a clear oil. C$_{12}$H$_{17}$NO$_3$ (223.27). ES-MS (m/z): found 224.12 (M+H). TLC: Rf=0.3 (20% ethylacetate in hexane). $^1$HNMR (400 MHz, CDCl$_3$) δ ppm, 1.52 (9H, s), 2.05 (1H, bs), 4.64 (2H, s), 6.58 (1H, bs), 7.01 (1H, d, J=7.2 Hz), 7.20-7.25 (2H, m), 7.40 (1H, s).

Preparation of Methanesulfonic Acid 3-tert-butoxycarbonylamino-benzyl ester (13)

To a stirred mixture of (3-Hydroxymethyl-phenyl)carbamic acid tert-butyl ester (12, 11.36 g, 51.1 mmol) and triethylamine (8.6 ml, 61.29 mmol) in dichloromethane (25 ml) was added dropwise methanesulfonyl chloride (3.04 g) with ice-cooling, and then the mixture was stirred at 0° C. for 0.5 hour and then at RT overnight. The produced precipitate was filtered and washed with dichloromethane. The combined filtrate and washings were concentrated and purified by column chromatography using 1% ethylacetate in dichloromethane to afford title compound (13) as a thick oil (6.1 g, 40%) having a melting point 75-76° C. C13H19NO5S (301.36). ES-MS (m/z): found 302.1 (M+H). TLC: Rf=0.25 (5% ethylacetate in hexane). $^1$H-NMR (400 MHz, CDCl3) δ ppm, 1.29 (3H, t), 1.51 (9H, s), 3.07 (2H, s), 3.79 (2H, s), 4.18 (2H, q), 6.47 (1H, br s), 6.97-7.03 (1H, m), 7.23-7.30 (2H, m), 7.36 (1H, s).

Preparation of the common advanced intermediate 15, X=N; Y=C; X$_1$=O; n=2; R$_2$=R$_3$=H) (Scheme 3):

Preparation of [3-(6-Morpholin-4-yl-3',6'-dihydro-2$^1$H-[2,4']bipyridinyl-1'-ylmethyl)-phenyl]-carbamic acid tert-butyl ester (14A)

6-Morpholin-4-yl-1',2',3',6'-tetrahydro-[2,4']bipyridinyl hydrochloride salt (8A, 110 mg, 0.31 mmol) was taken in dichloromethane (6 mL) and DIPEA (0.2 mL, 0.93 mmol) was added. To this mixture, methanesulfonic acid 3-tert-butoxycarbonylamino-benzyl ester (13, 102 mg, 0.33 mmol) dissolved in dichloromethane (1 mL) was added slowly using a syringe. The reaction mixture was kept under stirring overnight and solvents were removed. The residue was purified by column chromatography using 10-20% ethylacetate in hexanes to afford the title compound 14A as pale yellow oil (50 mg, 25%). C26H34N4O3 (450.26). ES-MS (m/z) found: 450.26 (M+). $^1$H NMR (400 MHz, CDCl$_3$) δ 7.47 (dd, J=8.3, 7.6 Hz, 1H), 7.34 (d, J=9.2 Hz, 2H), 7.30-7.20 (m, 1H), 7.07 (d, J=7.6 Hz, 1H), 6.76 (d, J=7.5 Hz, 1H), 6.64 (s, 1H), 6.50 (t, J=8.2 Hz, 1H), 6.47 (s, 1H), 3.93-3.76 (m, 4H), 3.63 (s, 2H), 3.58-3.48 (m, 4H), 3.21 (s, 2H), 2.72 (d, J=5.4 Hz, 2H), 2.64 (s, 2H), 1.53 (s, 9H).

Preparation of 3-(6-Morpholin-4-yl-3',6'-dihydro-2'H-[2,4']bipyridinyl-1'-ylmethyl)-phenylamine (15A) (X=N; Y=C; $X_1$=O; n=2; $R_2$=$R_3$=H)

[3-(6-Morpholin-4-yl-3',6'-dihydro-2'H-[2,4']bipyridinyl-1'-ylmethyl)-phenyl]-carbamic acid tert-butyl ester (14A, 50 mg, 0.11 mmol) was dissolved in dichloromethane (2 mL) and stirred with 4% HCl in dioxane for 2 hours at room temperature. When TLC indicated the reaction completion, the solvents were removed and triturated with cold ether to get the title compound, 15A as a white solid which was used in the next step as is. C21H26N4O (350.46). ES-MS (m/z): found 351.2 (M+H). $^1$H NMR (400 MHz, DMSO-D6) δ 7.89-7.76 (m, 1H), 7.69 (d, J=18.6 Hz, 1H), 7.55 (m, 3H), 6.86 (d, J=7.4 Hz, 1H), 6.80 (d, J=8.6 Hz, 1H), 6.57 (s, 1H), 4.46 (s, 3H), 3.91-3.67 (m, 7H), 3.48-3.40 (m, 6H), 3.20 (s, 1H), 2.84 (s, 2H).

Example 1, 1-Ethyl-3-[3-(6-morpholin-4-yl-3',6'-dihydro-2'H-[2,4']bipyridinyl-1'-ylmethyl)phenyl]urea, Compound 16A (X=N: Y=C; $X_1$=O; n=2; $R_2$=$R_3$=H: R5=ethyl, Scheme 3)

The hydrochloride salt of 3-(6-Morpholin-4-yl-3',6'-dihydro-2'H-[2,4']bipyridinyl-1'-ylmethyl)-phenylamine (15A, 68 mg, 0.19 mmol) was taken in dichloromethane (6 mL) and triethylamine (55 μL) was added and stirred for 5 min. Then ethylisocyanate (14 μL, 0.19 mmol) was added drop wise at room temperature and stirred overnight. The solvents were removed and purified by column chromatography using 5-10% methanol in dichloromethane system. The title compound 16A was isolated as a pale yellow solid after removal of the solvents and dried under high vacuum. Yield: 45 mg, 50%. C24H31N5O2 (421.54). ES-MS (m/z): found 422.2 (M+H). $^1$H NMR (400 MHz, CDCl$_3$) δ 7.45 (t, J=7.9 Hz, 1H), 7.30-7.16 (m, 3H), 7.02 (d, J=7.3 Hz, 1H), 6.73 (d, J=7.6 Hz, 1H), 6.69-6.68 (m, 1H), 6.61 (s, 1H), 6.49 (d, J=8.4 Hz, 1H), 5.26 (d, J=8.2 Hz, 1H), 3.92-3.74 (m, 4H), 3.52 (m, 6H), 3.16 (s, 2H), 2.85 (t, J=5.8 Hz, 2H), 2.69 (d, J=5.3 Hz, 2H), 2.60 (s, 2H), 1.22-1.05 (t, 3H).

Example 2, 1-Cyclohexyl-3-[3-(6-morpholin-4-yl-3',6'-dihydro-2'H-[2,4']bipyridinyl-1'-ylmethyl)-phenyl]-urea 16B (X=N; Y=C; $X_1$=O; n=2; $R_2$=$R_3$=H: R5=cyclohexyl, Scheme 3)

The hydrochloride salt (15A, 68 mg, 0.19 mmol) was taken in dichloromethane (6 mL) and triethylamine (55 μL) was added and stirred for 5 min. Then cyclohexyl-isocyanate (25 μL, 0.19 mmol) was added drop wise at room temperature and stirred overnight. The solvents were removed and purified by column chromatography using 5-10% methanol in dichloromethane system. The title compound 16B was isolated as a yellow solid after removal of the solvents and dried under high vacuum. Yield: 36 mg, 40%. C28H37N5O2 (475.63). ES-MS (m/z), found: 476.2 (M+H). $^1$HNMR: $^1$H NMR (400 MHz, CDCl$_3$) δ 7.49-7.39 (m, 1H), 7.35-7.11 (m, 4H), 7.01 (d, J=7.4 Hz, 1H), 6.74 (t, J=9.8 Hz, 1H), 6.60 (s, 1H), 6.49 (d, J=8.4 Hz, 1H), 5.31 (d, J=7.8 Hz, 1H), 3.94-3.71 (m, 4H), 3.71-3.39 (m, 7H), 3.17 (d, J=2.6 Hz, 2H), 2.70 (t, J=5.6 Hz, 2H), 2.61 (s, 2H), 1.92 (d, J=9.2 Hz, 2H), 1.65 (dd, J=9.5, 3.9 Hz, 2H), 1.55 (d, J=12.6 Hz, 1H), 1.42-1.21 (m, 2H), 1.21-1.00 (m, 3H).

Example 3, 1-Cyclopropyl-3-[3-(6-morpholin-4-yl-3',6'-dihydro-2'H-[2,4']bipyridinyl-1'-ylmethyl)-phenyl]-urea; Compound 16C (X=N; Y=C; $X_1$=O; n=2; $R_2$=$R_3$=H: R5=cyclopropyl, Scheme 3)

The hydrochloride salt (15A, 101 mg, 0.206 mmol) was taken in dichloromethane (6 mL) and triethylamine (15 μL) was added and stirred for 5 min. Then cyclopropylisocyanate (22 μL, 0.19 mmol) was added drop wise at room temperature and stirred overnight. The solvents were removed and purified by column chromatography using 5-10% methanol in dichloromethane system. The title compound 16C was isolated as a yellow solid after removal of the solvents and dried under high vacuum. Yield: 30 mg, 25%. C25H31N5O2 (433.55). ES-MS (m/z) found: 434.3 (M+H). $^1$H NMR (400 MHz, CDCl$_3$) δ 7.45 (t, J=7.9 Hz, 1H), 7.30-7.16 (m, 3H), 7.02 (d, J=7.3 Hz, 1H), 6.73 (d, J=7.6 Hz, 1H), 6.69-6.68 (m, 1H), 6.61 (s, 1H), 6.49 (d, J=8.4 Hz, 1H), 5.26 (d, J=8.2 Hz, 1H), 3.97 (dd, J=13.5, 6.6 Hz, 1H), 3.92-3.74 (m, 4H), 3.52 (m, 6H), 3.16 (s, 2H), 2.69 (d, J=5.3 Hz, 2H), 2.60 (s, 2H), 1.25 (d, J=22.1 Hz, 2H), 0.93-0.78 (m, 2H).

Preparation of 2-bromo-6-(piperidin-1-yl)pyridine, 6B (X=N; Y=$X_1$=C; n=2, Scheme 1)

In a 100 mL round bottom flask 2,6-dibromopyridine (1 g, 4.22 mmol), piperidine (0.395 g, 4.64 mmol), anhydrous potassium phosphate (0.896 g, 4.22 mmol) were taken in dry 1,4-Dioxane (60 ml) and reaction was heated at 105° C. under inert conditions for 16 h, cooled to room temp, solvents were removed under vacuum, residue was diluted with water, partitioned in DCM: Water, washed with brine, the organic layer was dried over sodium sulfate, filtered and concentrated under vacuum to give crude product, purified by flash chromatography using silica gel column (8:2 Hex/EtOAc) to give pure 2-bromo-6-(piperidin-1-yl)pyridine 6B (894 mg, 88 percent yield). C10H13BrN2 (241.13). ES-MS (m/z), found: 263.2 (M+Na). $^1$HNMR (400 MHz, CDCl$_3$) δ ppm 7.23 (dd, J=8 Hz, J=7 Hz, 1H); 6.6 (d, J=8 Hz, 1H); 6.49 (d, J=8 Hz, 1H); 3.53-3.50 (m, 4H); 1.66-1.59 (m, 6H).

Preparation of tert-butyl 4-(6-(piperidin-1-yl)pyridin-2-yl)-5,6-dihydropyridine-1(2H)-carboxylate, 7B (X=N; Y=$X_1$=C; n=2)

Tert-butyl 4-(4,4,5,5-tetramethyl-1,3,2-dioxaborolan-2-yl)-5,6-dihydropyridin-1(2H)-carboxylate (3) (338 mg, 1.09 mmol), 2-bromo-6-(piperidin-1-yl)pyridine (238 mg, 1.0 mmol), Pd(dppf)Cl$_2$ (40 mg, 0.05 mmol), and Cs$_2$CO$_3$ (1.0 g, 3.0 mmol) were added to toluene (10 mL) and purged with nitrogen. The resultant was stirred at 100° C. overnight. After the reaction mixture was cooled, it was purified by silica gel column chromatography using 5-10% ethylacetate in hexane system to give the title compound 7B (140 mg, 42%). C20H29N3O2 (343.46). ES-MS (m/z), found: 364.1 (M+Na). $^1$H NMR (400 MHz, CDCl$_3$) δ 7.52-7.37 (m, 1H), 6.64 (dd, J=12.1, 5.4 Hz, 2H), 6.54 (d, J=8.5 Hz, 1H), 4.13 (dd, J=12.1, 5.0 Hz, 2H), 3.63 (d, J=5.6 Hz, 2H), 3.55 (s, 4H), 2.61 (d, J=1.6 Hz, 2H), 1.66 (d, J=8.9 Hz, 6H), 1.49 (d, J=4.0 Hz, 9H).

Preparation of 2-(piperidin-1-yl)-6-(1,2,3,6-tetrahydropyridin-4-yl)pyridine hydrochloride salt, 8B (X=N; Y=$X_1$=C; n=2)

Tert-butyl 4-(6-(piperidin-1-yl)pyridin-2-yl)-5,6-dihydropyridine-1(2H)-carboxylate (120 mg) was stirred with 4%

HCl in dioxane (10 ml) for 16 hours and removed solvents under reduced pressure. The resulting white solid, 2-(piperidin-1-yl)-6-(1,2,3,6-tetrahydro-pyridin-4-yl)pyridine hydrochloride salt was triturated with dichloromethane and ether to give 8B as off-white solid and used as it is in the next step without further purification. C15H22ClN3 (279.81). ES-MS (m/z), found: 280.5 (M+H). $^1$H NMR (400 MHz, DMSO-D6) δ 9.42 (s, 2H), 7.55 (dt, J=46.4, 21.3 Hz, 1H), 6.98-6.75 (m, 2H), 6.61 (s, 1H), 3.76 (m, 2H), 3.53 (m, 4H), 3.24 (s, 2H), 2.69 (t, J=9.5 Hz, 2H), 1.61-1.42 (m, 6H).

Preparation of tert-butyl 3-((4-(6-(piperidin-1-yl)pyridin-2-yl)-5,6-dihydropyridin-1(2H)-yl)methyl) phenylcarbamate, 14B (X=N; Y=X$_1$=C; n=2; R$_2$=R$_3$=H)

2-(piperidin-1-yl)-6-(1,2,3,6-tetrahydro-pyridin-4-yl) pyridine hydrochloride salt (120 mg, 0.38 mmol) was dissolved in dichloromethane (6 mL) and triethylamine (0.3 mL) was added stirred for 10 min. Methanesulfonic acid 3-tert-butoxycarbonylamino-benzyl ester (13, R$_2$=R$_3$=H), 138 mg, 0.46 mmol) was added and stirred for 2 additional hours. Reaction was monitored by TLC and when product formation was complete, removed solvents under reduced pressure and purified by silica gel column using 20-50% ethylacetate in hexanes to afford the title compound 14B (100 mg, 40%) as pale yellow solid. C27H36N4O2 (448.60). ES-MS (m/z), found: 470.3 (M+Na). $^1$H NMR (400 MHz, CDCl$_3$) δ 7.41 (dd, J=8.4, 7.5 Hz, 1H), 7.34 (s, 2H), 7.31-7.22 (m, 1H), 7.07 (d, J=7.7 Hz, 1H), 6.74-6.61 (m, 2H), 6.52 (d, J=8.5 Hz, 1H), 6.46 (s, 1H), 3.63 (s, 2H), 3.55 (s, 4H), 3.21 (s, 2H), 2.73 (s, 2H), 2.64 (s, 2H), 1.64 (s, 6H), 1.51 (s, J=11.9 Hz, 9H).

Preparation of 3-((4-(6-(piperidin-1-yl)pyridin-2-yl)-5,6-dihydropyridin-1(2H)-yl)methyl)aniline hydrochloride salt, 15B (X=N; Y=X$_1$=C; n=2; R$_2$=R$_3$=H)

Tert-butyl 3-((4-(6-(piperidin-1-yl)pyridin-2-yl)-5,6-dihydropyridin-1(2H)-yl)methyl) phenylcarbamate 14B (510 mg, 1.14 mmol) was stirred with 4% HCl in Dioxane (10 ml) for 16 hours and removed solvents under reduced pressure. The resulting white solid was triturated with dichloromethane and ether to give the title compound 15B as nice white solid and used as it is in the next step without further purification. C22H29ClN4 (384.95). ES-MS (m/z), found: 385.5 (M+H). $^1$H NMR (400 MHz, DMSO-D6) δ 7.72 (d, J=7.8 Hz, 1H), 7.62 (s, 1H), 7.59-7.51 (m, 3H), 7.45 (d, J=9.1 Hz, 1H), 6.82 (dd, J=11.3, 8.1 Hz, 2H), 6.56 (s, 1H), 4.45 (s, 3H), 3.71 (dd, J=40.9, 23.6 Hz, 2H), 3.54 (m, 4H), 3.27 (d, J=58.2 Hz, 1H), 2.84 (s, 2H), 1.56 (d, J=2.6 Hz, 8H).

Example 4, 1-Ethyl-3-[3-(6-piperidine-1-yl-3',6'-dihydro-2'H-[2,4']bipyridinyl-1'-ylmethyl)-phenyl]-urea, Compound 16D (X=N: Y=X$_1$=C; n=2; R$_2$=R$_3$=H: R5=ethyl, Scheme 3)

3-((4-(6-(Piperidin-1-yl)pyridin-2-yl)-5,6-dihydropyridin-1(2H)-yl)methyl)aniline hydrochloride salt, 15B (80 mg, 0.19 mmol) was taken in dichloromethane (4 mL) and triethylamine (83 uL, 0.57 mmol) was added and stirred for 5 min. Then ethylisocyanate (21 uL, 0.28 mmol) was added drop wise at room temperature and stirred overnight. The solvents were removed and purified by column chromatography using 5-10% methanol in ethylacetate system. The title compound 16D was isolated as a yellow solid after removal of the solvents and dried under high vacuum. Yield: 32 mg, 43%. C25H33N5O (419.56). ES-MS (m/z), found: 420.6 (M+H). $^1$H NMR (400 MHz, CDCl$_3$) δ 7.53 (s, 1H), 7.49-7.35 (m, 2H), 7.31 (s, 1H), 7.21 (t, J=7.8 Hz, 1H), 6.99 (d, J=7.4 Hz, 1H), 6.62 (d, J 7.4 Hz, 1H), 6.54 (t, J=6.3 Hz, 2H), 5.69 (s, 1H), 3.67 (s, 2H), 3.53 (s, 4H), 3.30-3.17 (m, 4H), 2.85 (t, J=5.8 Hz, 2H), 2.66 (d, J=13.8 Hz, 2H), 1.64 (s, 6H), 1.22-1.05 (m, 3H).

Example 5, 1-Cyclohexyl-3-[3-(6-piperidine-1-yl-3',6'-dihydro-2'H-[2,4']bipyridinyl-1'-ylmethyl)-phenyl]-urea, Compound 16E (X=N: Y=X$_1$=C; n=2; R$_2$=R$_3$=H: R5=cyclohexyl, Scheme 3)

3-((4-(6-(piperidin-1-yl)pyridin-2-yl)-5,6-dihydropyridin-1(2H)-yl)methyl)aniline hydrochloride salt, 15B (78 mg, 0.19 mmol) was taken in dichloromethane (4 mL) and triethylamine (83 μL, 0.57 mmol) was added and stirred for 5 min. Then cyclohexylisocyanate (36 μL, 0.28 mmol) was added drop wise at room temperature and stirred overnight. The solvents were removed and purified by column chromatography using 100% ethylacetate system. The title compound 16E was isolated as a yellow solid after removal of the solvents and dried under high vacuum. Yield: 60 mg, 62%. C29H39N5O (473.65). ES-MS (m/z), found: 474.32 (M+H). $^1$H NMR (400 MHz, CDCl$_3$) δ 7.48-7.35 (m, 1H), 7.29 (dd, J=11.1, 5.2 Hz, 3H), 7.20 (t, J=7.8 Hz, 1H), 7.00 (d, J=7.5 Hz, 1H), 6.66-6.56 (m, 2H), 6.52 (d, J=8.4 Hz, 1H), 5.38 (d, J=7.8 Hz, 1H), 3.74-3.48 (m, 8H), 3.17 (s, 2H), 2.71 (t, J=5.5 Hz, 2H), 2.61 (s, 2H), 1.91 (d, J=9.3 Hz, 2H), 1.80-1.46 (m, 9H), 1.45-1.22 (m, 2H), 1.22-1.01 (m, 2H).

Example 6, 1-Cyclopropyl-3-[3-(6-piperidin-1-yl-3',6'-dihydro-2'H-[2,4']bipyridinyl-1'-ylmethyl)-phenyl]-urea, Compound 16F (X=N: Y=X$_1$=C; n=2; R$_2$=R$_3$=H: R5=cyclopropyl, Scheme 3)

3-((4-(6-(piperidin-1-yl)pyridin-2-yl)-5,6-dihydropyridin-1(2H)-yl)methyl)aniline hydrochloride salt, 15B (91 mg, 0.186 mmol) was taken in a mixture of THF (2 mL) and dichloromethane (4 mL) and triethylamine (100 μL, 0.74 mmol) was added and stirred for 5 min. Then cyclopropylisocyanate (20 μL, 0.28 mmol) was added drop wise at room temperature and stirred overnight. The solvents were removed and purified by column chromatography using 5-10% methanol in dichloromethane system. The title compound 16F was isolated as a yellow solid after removal of the solvents and dried under high vacuum. Yield: 35 mg, 40%. C26H33N5O (431.57). ES-MS (m/z), found: 432.2 (M+H). $^1$H NMR (400 MHz, CDCl$_3$) δ 7.47 (d, J=9.1 Hz, 1H), 7.40 (dd, J=8.4, 7.5 Hz, 1H), 7.32 (t, J=1.8 Hz, 1H), 7.30-7.21 (m, 1H), 7.13 (s, 1H), 7.05 (d, J=7.6 Hz, 1H), 6.64 (dd, J=7.6, 5.5 Hz, 2H), 6.52 (6, J=8.4 Hz, 1H), 5.21 (s, 1H), 3.60 (s, 2H), 3.58-3.57 (m, 4H), 3.19 (d, J=3.3 Hz, 2H), 2.71 (t, J=5.7 Hz, 2H), 2.65-2.54 (m, 3H), 1.63 (s, 6H), 0.87-0.75 (m, 2H), 0.65-0.58 (m, 2H).

Preparation of 1-(6-Bromo-pyridin-2-yl)-4-methyl-piperazine, 6C (X=N; Y=C; X$_1$=N—CH$_3$; n=2, Scheme 1)

In a 100 mL round bottom flask 2,6-dibromopyridine (1 g, 4.22 mmol), N-methylpiperazine (464 mg, 4.64 mmol), anhydrous potassium phosphate (0.896 g, 4.22 mmol) were taken in dry 1,4-Dioxane (60 ml) and reaction was heated at 105° C. under inert conditions for 16 h, cooled to room temp, solvents were removed under vacuum, residue was diluted with water, partitioned in DCM: Water, washed with brine, the organic layer was dried over sodium sulfate, filtered and concentrated under vacuum to give crude product, purified by flash chromatography using silica gel column (8:2 Hex/EtOAc; 80 g) to give pure 1-(6-Bromopyridin-2-yl)-4-methyl-piperazine 6C (0.90 g, 88%). C10H14BrN3 (256.14). ES-MS (m/z), found: 257.04 (M+H). $^1$H NMR (400 MHz, CDCl$_3$) δ 7.25 (dd, J=8.4, 7.5 Hz, 1H), 6.72 (d, J=7.4 Hz, 1H), 6.49 (d, J=8.4 Hz, 1H), 3.67-3.45 (m, 4H), 2.57-2.41 (m, 4H), 2.31 (d, J=2.7 Hz, 3H).

Preparation of 6-(4-Methyl-piperazin-1-yl)-3',6'-dihydro-2'H-[2,4']bipyridinyl-1'-carboxylic acid tert-butyl ester, 7C (X=N; Y=C; X$_1$=N—CH$_3$; n=2)

Tert-butyl 4-(4,4,5,5-tetramethyl-1,3,2-dioxaborolan-2-yl)-5,6-dihydropyridin-1(2H)-carboxylate, 3 (1.1 g, 3.5 mmol), 1-(6-bromopyridin-2-yl)-4-methylpiperazine, 6C (828 mg, 3.2 mmol), Pd(PPh3)4 (187 mg, 0.16 mmol), and K$_2$CO$_3$ (1.4 g, 9.6 mmol) were added to 1,4-dioxane (30 mL) and water (3 mL) and purged with nitrogen. The reaction mixture was then stirred at 100° C. overnight. After the reaction mixture was cooled, it was purified by silica gel column chromatography to give title compound 7C as a pale yellow solid (830 mg, 42%). C20H30N4O2 (358.48). ES-MS (m/z), found: 259.2 (M+H). $^1$H NMR (400 MHz, DMSO-D6) δ 7.73-7.53 (m, 1H), 6.93-6.83 (m, 2H), 6.67 (s, 1H), 4.44 (t, J=34.2 Hz, 656H), 3.69 (d, J=33.1 Hz, 2H), 3.47 (dd, J=29.6, 11.8 Hz, 2H), 3.36-3.18 (m, 4H), 3.01 (dt, J=28.6, 14.5 Hz, 2H), 2.72 (dd, J=26.6, 15.1 Hz, 6H), 2.49 (s, 3H), 1.39 (s, J=4.0 Hz, 9H).

Preparation of 6-(4-Methyl-piperazin-1-yl)-1',2',3',6'-tetrahydro-[2,4']bipyridinyl hydrochloride, 8C (X=N; Y=C; X$_1$=N—CH$_3$; n=2)

6-(4-Methyl-piperazin-1-yl)-3',6'-dihydro-2'H-[2,4']bipyridinyl-1'-carboxylic acid tert-butyl ester (7C, 750 mg) was dissolved in dichloromethane (5 mL) and stirred with 4% HCl in Dioxane (10 ml) for 16 hours and removed solvents under reduced pressure. The resulting white solid, hydrochloride salt (8C) was triturated with dichloromethane and ether to give nice solid and used as it is in the next step without further purification. C15H23C1N4 (294.82). ES-MS (m/z): found 296.1 (M+H). $^1$H NMR (400 MHz, DMSO-D6) δ 9.53 (s, 2H), 7.73-7.53 (m, 1H), 6.93-6.83 (m, 2H), 6.67 (s, 1H), 4.44 (t, J=34.2 Hz, 656H), 3.69 (d, J=33.1 Hz, 2H), 3.47 (dd, J=29.6, 11.8 Hz, 2H), 3.36-3.18 (m, 4H), 3.01 (dt, J=28.6, 14.5 Hz, 2H), 2.72 (dd, J=26.6, 15.1 Hz, 6H), 2.49 (s, 3H).

Preparation of {3-[6-(4-Methyl-piperazin-1-yl)-3',6'-dihydro-2'H-[2,4']bipyridinyl-1'-ylmethyl]-phenyl}-carbamic acid tert-butyl ester, 14C (X=N; Y=C; X$_1$=N—CH$_3$; n=2; R$_2$=R$_3$=H)

The hydrochloride salt (8C, 1.1 g, 3.0 mmol) was dissolved in dichloromethane (40 mL) and triethylamine (1.2 mL) was added stirred for 10 min. Methanesulfonic acid 3-tert-butoxycarbonylamino-benzyl ester (13) (R$_2$=R$_3$=H), 1.1 g, 3.6 mmol) was added and stirred for 2 additional hours. Reaction was monitored by TLC and when product formation was complete, removed solvents under reduced pressure and purified by silica gel column using 5-10% methanol in dichloromethane to afford the title compound 14C (580 mg, 66%) as pale yellow solid. C27H37N5O2 (463.61). ES-MS (m/z), found: 464.3 (M+H). $^1$H NMR (400 MHz, CDCl$_3$) δ 8.23 (s, 1H), 7.69-7.36 (m, 3H), 7.18 (t, J=7.9 Hz, 1H), 7.00 (d, J=7.3 Hz, 1H), 6.68 (d, J=7.6 Hz, 1H), 6.65-6.40 (m, 2H), 6.10 (s, 1H), 3.77 (s, 2H), 3.63 (m, 4H), 3.37 (d, J=8.9 Hz, 2H), 3.24 (dd, J=13.1, 6.9 Hz, 2H), 2.74 (s, 2H), 2.63 (s, 4H), 2.43 (s, 3H), 1.32 (s, J=4.0 Hz, 9H).

Preparation of 3-[6-(4-Methyl-piperazin-1-yl)-3',6'-dihydro-2'H-[2,4']bipyridinyl-1'-ylmethyl]-phenylamine hydrochloride, 15C (X=N; Y=C; X$_1$=N—CH$_3$; n=2; R$_2$=R$_3$=H)

{3-[6-(4-Methyl-piperazin-1-yl)-3',6'-dihydro-2'H-[2,4']bipyridinyl-1'-ylmethyl]-phenyl})-carbamic acid tert-butyl ester 14C (920 mg, 1.98 mmol) was dissolved in dichloromethane (15 mL) and stirred with 4% HCl in Dioxane (10 ml) for 16 hours and removed solvents under reduced pressure. The resulting white solid, hydrochloride salt (15C) was triturated with dichloromethane and ether to give nice solid and used as it is in the next step without further purification. C22H30C1N5 (399.96). ES-MS (m/z), found: 400.22 (M+H). $^1$H NMR (400 MHz, DMSO) δ 8.23 (s, 1H), 7.69-7.36 (m, 1H), 7.18 (t, J=7.9 Hz, 1H), 7.00 (d, J=7.3 Hz, 1H), 6.93-6.83 (m, 2H), 6.68 (d, J=7.6 Hz, 1H), 6.65-6.40 (m, 2H), 6.10 (s, 1H), 4.45 (s, 3H), 3.77 (s, 2H), 3.63 (m, 4H), 3.37 (d, J=8.9 Hz, 2H), 3.24 (dd, J=13.1, 6.9 Hz, 2H), 2.74 (s, 2H), 2.63 (s, 4H), 2.43 (s, 3H).

Example 7: 1-Ethyl-3-{3-[6-(4-methyl-piperazin-1-yl)-3',6'-dihydro-2'H-[2,4']bipyridinyl-1'-ylmethyl]-phenyl}-urea 16G (X=N: Y=C; X$_1$=N—CH3; n=2; R$_2$=R$_3$=H: R5=ethyl, Scheme 3)

The hydrochloride salt (15C, 150 mg, 0.28 mmol) was taken in dichloromethane (5 mL) and triethylamine (200 μL, 0.57 mmol) was added and stirred for 5 min. Then ethylisocyanate (70 μL, 0.28 mmol) was added drop wise at room temperature and stirred overnight. The solvents were removed and purified by column chromatography using 15% methanol in ethylacetate system. The title compound 16G was isolated as a yellow solid after removal of the solvents and dried under high vacuum. Yield: 85 mg, 50% C25H34N6O (434.58). ES-MS (m/z), found: 435.2 (M+H). $^1$H NMR (400 MHz, CDCl$_3$) δ 8.23 (s, 1H), 7.69-7.36 (m, 3H), 7.18 (t, J=7.9 Hz, 1H), 7.00 (d, J=7.3 Hz, 1H), 6.68 (d, J=7.6 Hz, 1H), 6.65-6.40 (m, 2H), 6.10 (s, 1H), 3.77 (s, 2H), 3.63 (m, 4H), 3.37 (d, J=8.9 Hz, 2H), 3.24 (dd, J=13.1, 6.9 Hz, 2H), 2.96 (s, 2H), 2.74 (s, 2H), 2.63 (s, 4H), 2.42 (s, 3H), 1.12 (t, J=7.2 Hz, 3H).

Example 8: 1-Cyclohexyl-3-{3-[6-(4-methyl-piperazin-1-yl)-3',6'-dihydro-2'H-[2,4']bipyridinyl-1'-ylmethyl]-phenyl}-urea, 16H (X=N: Y=C; X$_1$=N—CH3; n=2; R$_2$=R$_3$=H: R5=cyclohexyl, Scheme 3)

The hydrochloride salt (15C, 119 mg, 0.22 mmol) was taken in dichloromethane (5 mL) and triethylamine (200 uL, 0.57 mmol) was added and stirred for 5 min. Then cyclohexylisocyanate (32 uL, 0.44 mmol) was added drop wise at room temperature and stirred overnight. The solvents were removed and purified by column chromatography using 15% methanol in dichloromethane system. The title compound 16H was isolated as a yellow solid after removal of the solvents and dried under high vacuum. Yield: 75 mg, 50%. C29H40N6O (488.67). ES-MS (m/z), found: 489.3 (M+H). $^1$H NMR (400 MHz, CDCl$_3$) δ 7.51-7.34 (m, 2H), 7.34-7.18

(m, 2H), 7.13-6.95 (m, 2H), 6.70 (d, J=7.5 Hz, 1H), 6.59 (s, 1H), 6.53 (d, J=8.5 Hz, 1H), 5.24 (s, 1H), 3.62 (d, J=18.8 Hz, 6H), 3.24 (s, 2H), 2.79 (d, J=5.1 Hz, 2H), 2.66 (s, 2H), 2.54 (s, 4H), 2.36 (s, 3H), 1.92 (s, 2H), 1.67 (s, 2H), 1.56 (s, 2H), 1.38-1.05 (m, 7H).

Example 9: 1-Cyclopropyl-3-{3-[6-(4-methyl-piperazin-1-yl)-3',6'-dihydro-2'H-[2,4']bipyridinyl-1'-ylmethyl]-phenyl}-urea (16I) (X=N: Y=C; $X_1$=N—CH3; n=2; $R_2$=$R_3$=H: R5=cyclopropyl, Scheme 3)

The hydrochloride salt (15C, 110 mg, 0.20 mmol) was taken in dichloromethane (4 mL) and triethylamine (100 µL, 0.74 mmol) was added and stirred for 5 min. Then cyclopropylisocyanate (25 µL, 0.3 mmol) was added drop wise at room temperature and stirred overnight. The solvents were removed and purified by column chromatography using 5-10% methanol in dichloromethane with 2% aq. ammonia system. The title compound, 16I, was isolated as a yellow solid after removal of the solvents and dried under high vacuum. Yield: 35 mg, 40%. C26H34N6O (446.59), ES-MS (m/z), found: 447.28 (M+H). $^1$H NMR (400 MHz, CDCl$_3$) δ 8.23 (s, 1H), 7.69-7.36 (m, 3H), 7.18 (t, J=7.9 Hz, 1H), 7.00 (d, J=7.3 Hz, 1H), 6.68 (d, J=7.6 Hz, 1H), 6.65-6.40 (m, 2H), 6.10 (s, 1H), 3.90 (dd, J=13.5, 6.6 Hz, 1H), 3.77 (s, 2H), 3.63 (m, 4H), 3.37 (d, J=8.9 Hz, 2H), 3.24 (dd, J=13.1, 6.9 Hz, 2H), 2.96 (s, 2H), 2.63 (s, 4H), 2.42 (s, 3H), 1.25 (d, J=22.1 Hz, 2H), 0.93-0.78 (m, 2H).

IV. Evaluation of Biological Activity

Compounds described in the Examples above were tested for inhibition of IDO activity with IDO Kynurenine Assay with Human IDO1/HEK293 Cells.

Human ID01/HEK293 cells were seeded at 10,000 cells per 50 µL per well with RP Ml/phenol red free media containing 10% FBS in a 384-well black wall clear bottom tissue culture plate (Matrix Technologies LLC). 125 nL of certain concentration of compound was then added to each well using ECHO liquid handling systems. The cells were incubated for 20 hours in 37° C. incubator with 5% CO$_2$.

The compound treatments were stopped by adding trichloroacetic acid (Sigma-Aldrich) to a final concentration at 0.2%. The cell plate was further incubated at 50° C. for 30 minute. The equal volume supernatant (20 µL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound IC$_{50}$ values were calculated using the counts of 500 nM of a reference standard treatment as one hundred percent inhibition, and counts of no compound but DMSO treatment as zero percent inhibition.

TABLE 1

| | HEK Human IDO-1 | | | |
|---|---|---|---|---|
| | Primary SP | Primary CRC | | |
| Compounds | Basal_L-Kynurenine (IDO1 % inhib @ 10 µM) | Basal_L-Kynurenine IDO1 Rel IC50 | Basal_N-formyl-kyn IDO1 Rel IC50 | Basal_Viability Rel IC50 |
| Example 1 | >90% | <2.0 µM | <2.0 µM | >50 |
| Example 2 | >90% | <2.0 µM | <2.0 µM | >50 |
| Example 3 | >90% | <2.0 µM | <2.0 µM | >50 |
| Example 4 | >90% | <2.0 µM | <2.0 µM | >50 |
| Example 5 | >90% | <2.0 µM | <2.0 µM | >50 |
| Example 6 | >90% | <2.0 µM | <2.0 µM | >50 |
| Example 7 | <90% | >2.0 µM | >2.0 µM | >50 |
| Example 8 | <90% | >2.0 µM | >2.0 µM | >50 |
| Example 9 | <90% | >2.0 µM | >2.0 µM | >50 |

Definitions and Interpretation

The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. Embodiments were chosen and described in order to best explain the principles of the invention and the practical application, and to enable others of ordinary skill in the art to understand the invention for various embodiments with various modifications as are suited to the particular use contemplated. To the extent that the following description is of a specific embodiment or a particular use of the invention, it is intended to be illustrative only, and not limiting of the claimed invention.

The corresponding structures, materials, acts, and equivalents of all means or steps plus function elements in the claims appended to this specification are intended to include any structure, material, or act for performing the function in combination with other claimed elements as specifically claimed.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to combine, affect or connect such aspect, feature, structure, or characteristic with other embodiments, whether or not such connection or combination is explicitly described. In other words, any element or feature may be combined with any other element or feature in different embodiments, unless there is an obvious or inherent incompatibility between the two, or it is specifically excluded.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

The singular forms "a," "an," and "the" include the plural reference unless the context clearly dictates otherwise. The term "and/or" means any one of the items, any combination of the items, or all of the items with which this term is associated.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

As will also be understood by one skilled in the art, all ranges described herein, and all language such as "up to", "at least", "greater than", "less than", "more than", "or more", and the like, include the number(s) recited and such terms refer to ranges that can be subsequently broken down into sub-ranges as discussed above.

The invention claimed is:

1. A compound of formula I wherein:
X is N or CR;
Y is N or CR;
$Y_1$ is N or C;
R is H, halogen, optionally substituted C1-C3 alkyl or optionally substituted C1-C3 alkoxy;
$X_1$ is selected from $CH_2$, O, S or $NR_1$, where $R_1$ is H or C1-C3 alkyl;
n is selected from 1, 2 or 3;
$R_2$ and $R_3$ independently is H or C1-C2-alkyl or together with the carbon to which they are attached to form a C3-C4 cycloalkyl;
$R_4$ is —CONHR$_5$, —CSNHR$_5$, C(=NH)NHR$_5$, —SO$_2$R$_6$, —COR$_6$, optionally substituted C1-C6 alkyl, optionally substituted C3-C8 heteroaryl, optionally substituted C3-C8 alkylheteroaryl, optionally substituted C3-C8 alkoxylheteroaryl, optionally substituted C3-C8 heterocycle, optionally substituted C3-C8 alkylheterocycle or optionally substituted C3-C8 alkoxyheterocycle;
$R_5$ is optionally substituted C1-C6 alkyl, optionally substituted C2-C6 alkenyl, optionally substituted C2-C6 alkynyl, optionally substituted C3-C7 cycloalkyl, or optionally substituted C4-C7 cycloalkenyl; optionally substituted aryl, optionally substituted C7-C10 alkylaryl, optionally substituted C7-C10 alkoxyaryl, optionally substituted C3-C10 heteroaryl, optionally substituted C3-10-alkyl heteroaryl or C3-C8 heterocycle; and
$R_6$ is CF$_3$, optionally substituted C1-C5 alkyl, optionally substituted aryl, optionally substituted C7-C10 alkylaryl, optionally substituted C7-C10 alkoxyaryl, optionally substituted C3-C10 heteroaryl, optionally substituted C3-10-alkyl heteroaryl or C3-C8 heterocycle.

2. A compound of formula II:

wherein:
X is N;
$X_1$ is selected from CH2, O, or $NR_1$, where $R_1$ is H or C1-C3 alkyl;
$Y_1$ is N or C;
$R_2$ and $R_3$ independently is H or C1-C2-alkyl or together with the carbon to which they are attached to form a C3-C4 cycloalkyl;
$X_2$ is selected from O, S, NH;
$R_5$ is optionally substituted C1-C6 alkyl, optionally substituted C2-C6 alkenyl, optionally substituted C2-C6 alkynyl, optionally substituted C3-C7 cycloalkyl, or optionally substituted C4-C7 cycloalkenyl; optionally substituted aryl, optionally substituted C7-C10 alkylaryl, optionally substituted C7-C10 alkoxyaryl, optionally substituted C3-C10 heteroaryl, optionally substituted C3-10-alkyl heteroaryl or C3-C8 heterocycle.

3. The compound of claim 2 wherein one or more of the optional substitutions is chlorine, fluorine, methyl, methoxy, trifluoromethyl or trifluoromethoxy.

4. The compound of claim 2 which is N-[3-(6-Morpholin-4-yl-3',6'-dihydro-2'H-[2,4']bipyridinyl-1'-ylmethyl)-phenyl]-N'-p-tolyl-guanidine.

5. A compound of formula III:

wherein:

X is $CH_2$, O, S, or N—$R_1$, where $R_1$ is H or C1-C3 alkyl; and

R is optionally substituted C1-C6 alkyl, optionally substituted C2-C6 alkenyl, optionally substituted C2-C6 alkynyl, optionally substituted C3-C7 cycloalkyl, or optionally substituted C4-C7 cycloalkenyl; optionally substituted aryl, optionally substituted C7-C10 alkylaryl, optionally substituted C7-C10 alkoxyaryl, optionally substituted C3-C10 heteroaryl, optionally substituted C3-10-alkyl heteroaryl or C3-C8 heterocycle.

6. The compound of claim 1 which is one of:

1-ethyl-3-[3-(6-morpholin-4-yl-3',6'-dihydro-2'H-[2,4']bipyridinyl-1'-ylmethyl)-phenyl]-urea;

1-cyclohexyl-3-[3-(6-morpholin-4-yl-3',6'-dihydro-2'H-[2,4']bipyridinyl-1'-ylmethyl)-phenyl]-urea;

1-ethyl-3-[3-(6-piperidine-1-yl-3',6'-dihydro-2'H-[2,4']bipyridinyl-1'-ylmethyl)-phenyl]-urea;

1-cyclohexyl-3-[3-(6-piperidine-1-yl-3',6'-dihydro-2'H-[2,4']bipyridinyl-1'-ylmethyl)-phenyl]-urea;

1-cyclopropyl-3-[3-(6-piperidine-1-yl-3',6'-dihydro-2'H-[2,4']bipyridinyl-1'-ylmethyl)-phenyl]-urea;

1-cyclopropyl-3-[3-(6-morpholin-4-yl-3',6'-dihydro-2'H-[2,4']bipyridinyl-1'-ylmethyl)-phenyl]-urea;

1-cyclopropyl-3-[3-(6-piperzin-1-yl-3',6'-dihydro-2'H-[2,4']bipyridinyl-1'-ylmethyl)-phenyl]-urea;

1-cyclohexyl-3-[3-(6-piperzin-1-yl-3',6'-dihydro-2'H-[2,4']bipyridinyl-1'-ylmethyl)-phenyl]-urea;

1-ethyl-3-[3-(6-piperzin-1-yl-3',6'-dihydro-2'H-[2,4']bipyridinyl-1'-ylmethyl)-phenyl]-urea;

1-cyclopropyl-3-{3-[6-(4-methyl-piperazin-1-yl)-3',6'-dihydro-2'H-[2,4']bipyridinyl-1'-ylmethyl]-phenyl}-urea;

1-ethyl-3-{3-[6-(4-methyl-piperazin-1-yl)-3',6'-dihydro-2'H-[2,4']bipyridinyl-1'-ylmethyl]-phenyl}-urea;

1-cyclohexyl-3-{3-[6-(4-methyl-piperazin-1-yl)-3',6'-dihydro-2'H-[2,4']bipyridinyl-1'-ylmethyl]-phenyl}-urea;

1-(2,4-difluoro-phenyl)-3-[3-(6-morpholin-4-yl-3',6'-dihydro-2'H-[2,4']bipyridinyl-1'-ylmethyl)-phenyl]-urea;

1-(4-chloro-2-fluoro-phenyl)-3-[3-(6-morpholin-4-yl-3',6'-dihydro-2'H-[2,4']bipyridinyl-1'-ylmethyl)-phenyl]-urea;

1-(2-fluoro-phenyl)-3-[3-(6-morpholin-4-yl-3',6'-dihydro-2'H-[2,4']bipyridinyl-1'-ylmethyl)-phenyl]-urea;

1-[3-(6-morpholin-4-yl-3',6'-dihydro-2'H-[2,4']bipyridinyl-1'-ylmethyl)-phenyl]-3-p-tolyl-thiourea;

1-cyclohexyl-3-{3-[1-(6-morpholin-4-yl-3',6'-dihydro-2'H-[2,4']bipyridinyl-1'-yl)-ethyl]-phenyl}-urea;

1-cyclohexyl-3-{3-[1-(6-morpholin-4-yl-3',6'-dihydro-2'H-[2,4']bipyridinyl-1'-yl)-cyclopropyl]-phenyl}-urea;

1-(3-methyl-isoxazol-5-yl)-3-{3-[1-(6-morpholin-4-yl-3',6'-dihydro-2'H-[2,4']bipyridinyl-1'-yl)-cyclopropyl]-phenyl}-urea;

1-(3-Methyl-isoxazol-5-yl)-3-[3-(6-morpholin-4-yl-3',6'-dihydro-2'H-[2,4']bipyridinyl-1'-ylmethyl)-phenyl]-urea; or 1-(5-methyl-pyridin-2-yl)-3-[3-(6-morpholin-4-yl-3',6'-dihydro-2'H-[2,4']bipyridinyl-1'-ylmethyl)-phenyl]-urea.

7. A racemic mixture, a stereoisomer, an enantiomer, a tautomer or a pharmaceutically acceptable salt of a compound of claim 1.

8. A pharmaceutical composition comprising one or more compounds according to claim 1, and a pharmaceutically acceptable carrier or diluent.

9. A method for the treatment or prevention of any cancer, autoimmune disease, or viral infection that is sensitive to enzymatic activity of indoleamine 2,3-dioxygenase, comprising administering to a patient a therapeutically effective amount of a compound according to claim 1, or a composition of claim 8.

10. The method according to claim 9 further comprising administering to the patient a therapeutically effective amount of another therapeutic agent or an anti-tumor vaccine prior to, simultaneously with or subsequent to administration of the compound or composition.

11. A method of inhibiting activity of indoleamine 2,3-dioxygenase in vivo, ex vivo or in vitro, comprising contacting said indoleamine 2,3-dioxygenase with a compound of claim 1.

* * * * *